United States Patent [19]
Bilotti et al.

[11] Patent Number: 5,219,111
[45] Date of Patent: Jun. 15, 1993

[54] PNEUMATICALLY ACTUATED LINEAR STAPLING DEVICE

[75] Inventors: Federico Bilotti, Madeira; Mark Ortiz, Milford; Narinderjit S. Sambi, Maineville; Ronald R. Van Overloop, West Chester, all of Ohio

[73] Assignee: Ethicon, Inc., Somerville, N.J.

[21] Appl. No.: 898,257

[22] Filed: Jun. 15, 1992

Related U.S. Application Data

[63] Continuation of Ser. No. 667,776, Mar. 11, 1991, abandoned.

[51] Int. Cl.⁵ .................................. A61B 17/072
[52] U.S. Cl. ............................. 227/175; 227/19; 227/178
[58] Field of Search ............... 227/19, 175, 176, 177, 227/180, 181, 130, 142

[56] References Cited

U.S. PATENT DOCUMENTS

| | | | |
|---|---|---|---|
| 4,573,622 | 3/1986 | Green | 227/19 |
| 4,610,386 | 9/1986 | Augostini | 227/142 |
| 4,714,187 | 12/1987 | Green | 227/19 |
| 4,767,044 | 8/1988 | Green | 227/19 |
| 4,887,756 | 12/1989 | Puchy | 227/19 |
| 5,018,657 | 5/1991 | Pedlick et al. | 227/178 |

*Primary Examiner*—Douglas D. Watts
*Assistant Examiner*—Rinaldi Rada
*Attorney, Agent, or Firm*—Paul A. Coletti

[57] ABSTRACT

A pneumatic stapler which contains a mechanism for manual or automatic retaining pin placement. The automatic retaining pin is connected to a set of linkage plates actuable by a series of inflation of bladders in order to create instrument closure on tissue compression and simultaneously create pin placement. An optional manual, curved retaining pin is used in place of the automatic pin system. Further, because this instrument has a ramped anvil mechanism, adjustable staple height is derived. Controlled closure of the mechanism is provided with a detent spring and constant force springs. Upon stapling, the staple encounters an anvil with reduced size, which is kept closed by a latched retaining pin system to allow for reduced width of the anvil so that the stapling head becomes more versatile. Finally, after firing the staples, the mechanism is capable of rapid depressurization and simultaneous instrument opening by a spring return mechanism. A shaft connects the head to the handle allowing rotation and articulation in an universal joint or in two discrete locations, both with a locking system enabling the operator to choose angles at which to insert the instrument.

7 Claims, 12 Drawing Sheets

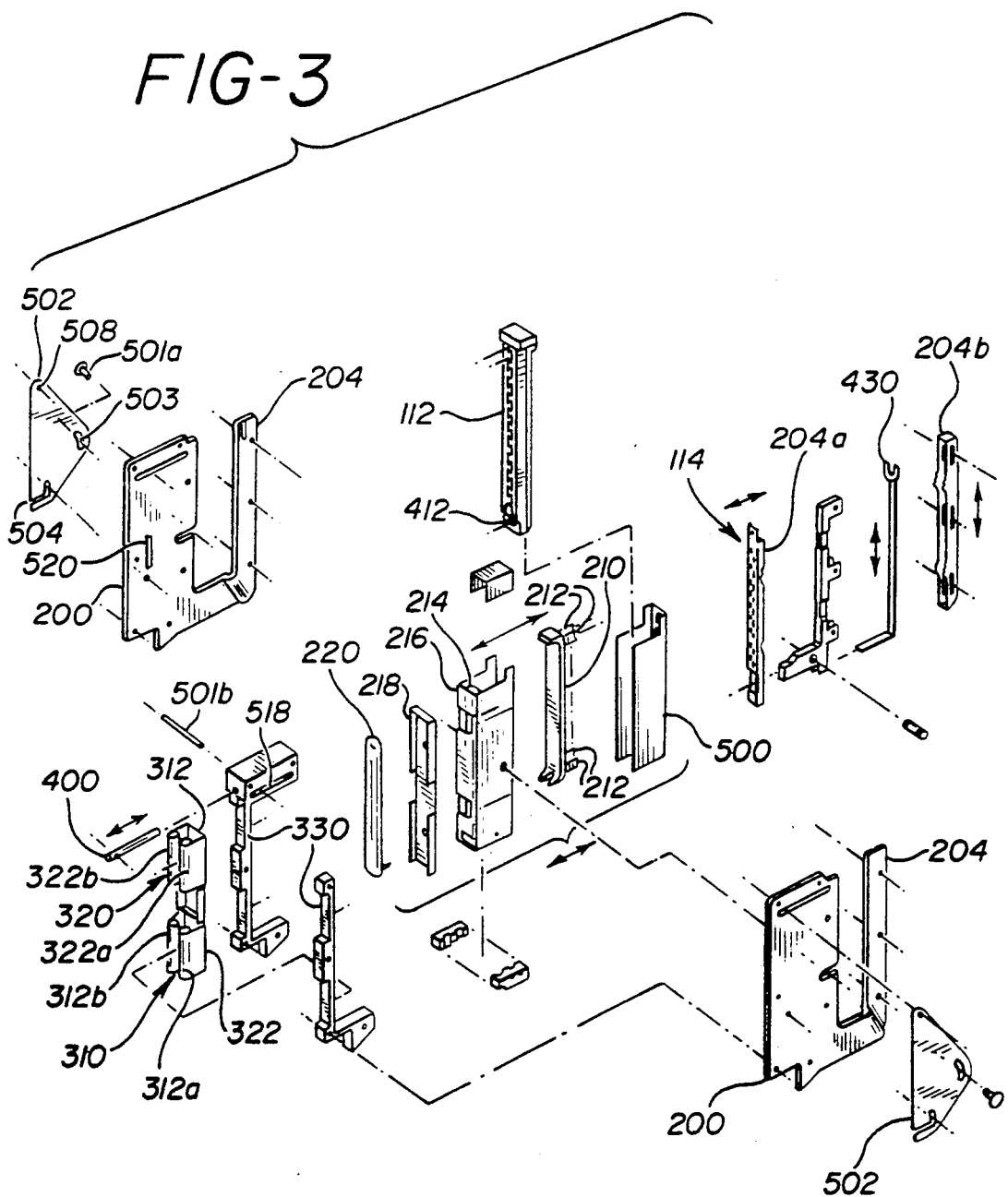

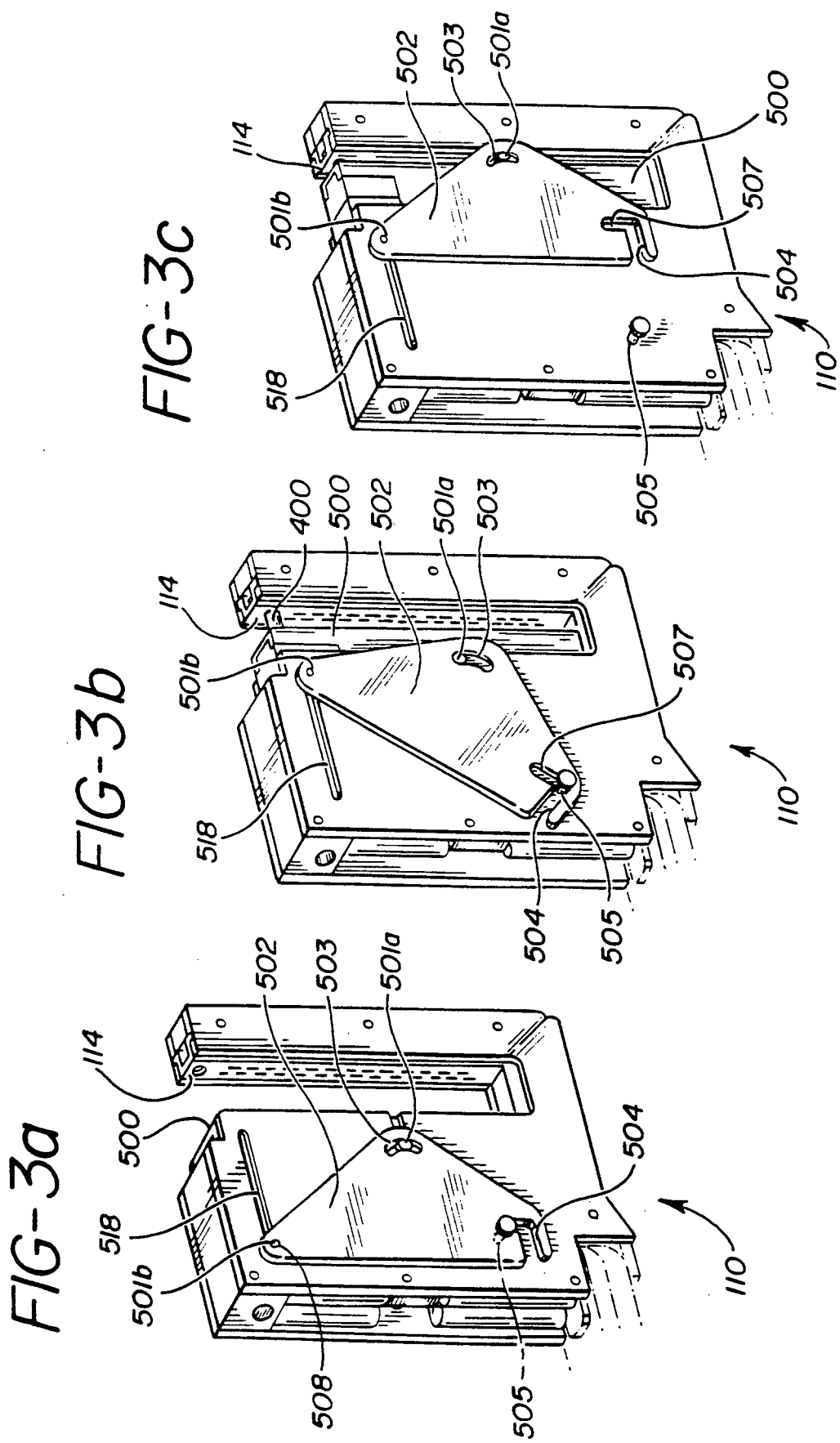

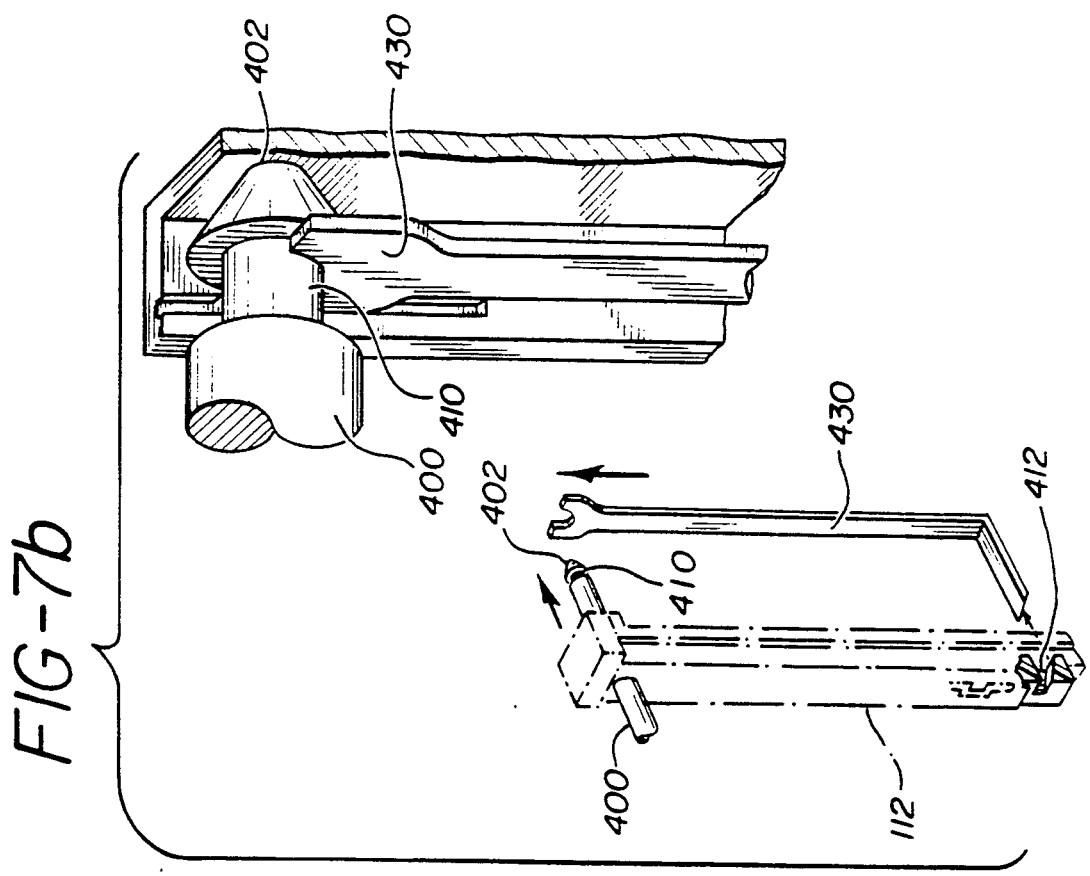
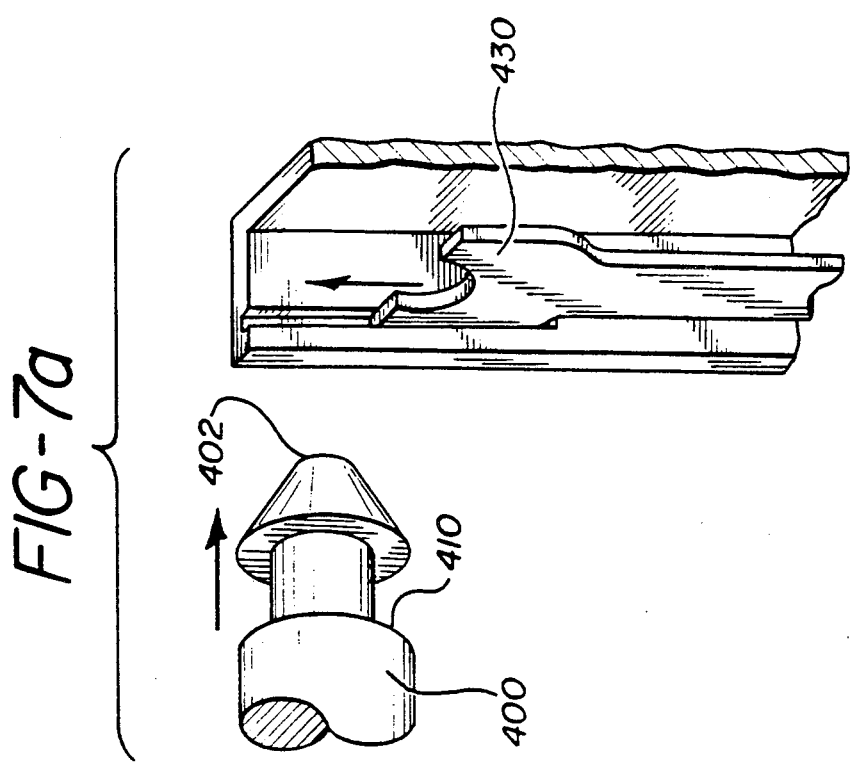

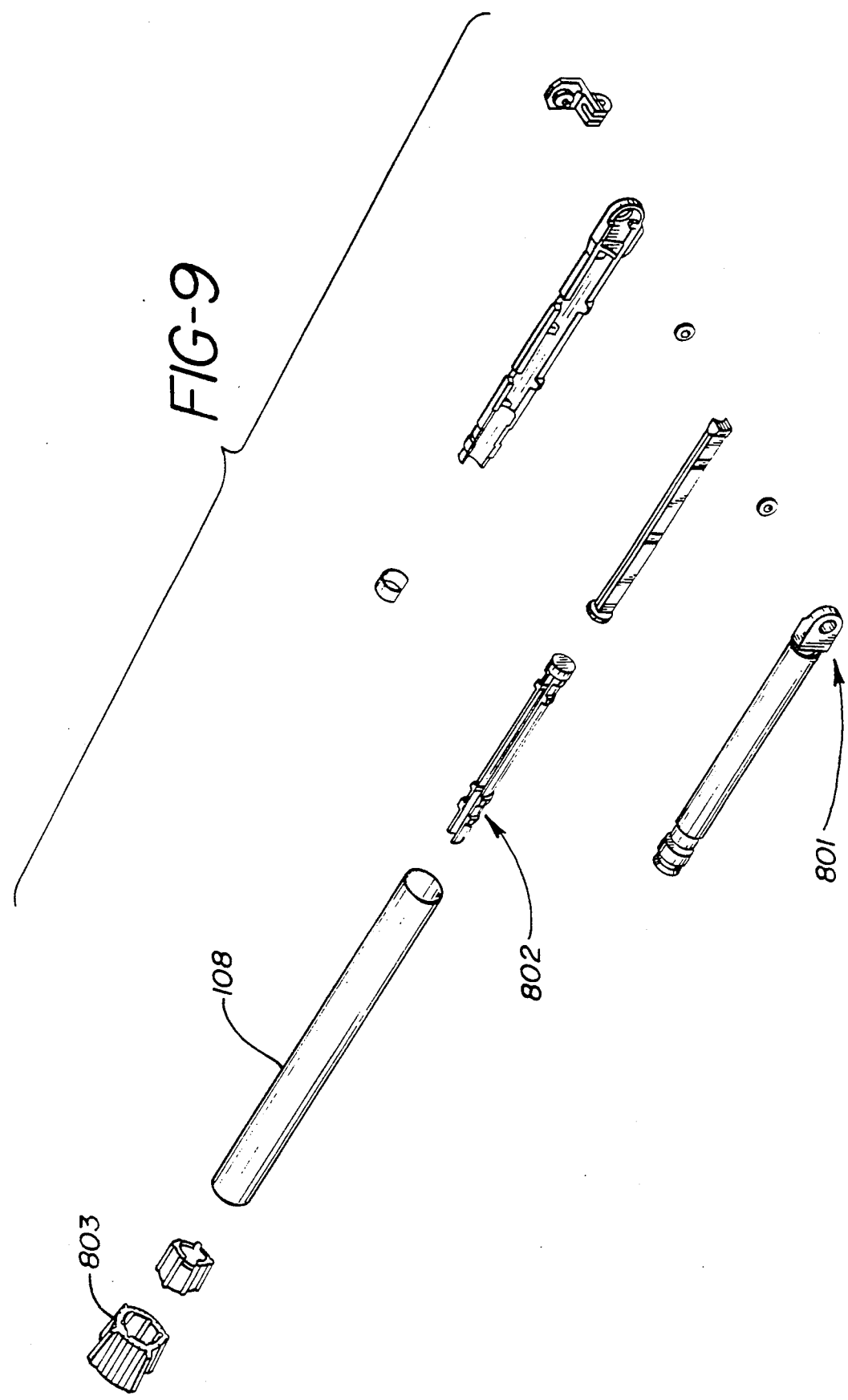

PNEUMATICALLY ACTUATED LINEAR STAPLING DEVICE

This is a continuation of application Ser. No. 667,776, filed Mar. 11, 1991, now abandoned, which is hereby incorporated by reference.

FIELD OF THE INVENTION

This invention relates to surgical staplers. More specifically, this invention relates to pneumatically actuated surgical stapling devices. Most specifically, this invention relates to improved aspects of pneumatically actuated linear stapling devices.

BACKGROUND OF THE INVENTION

One of the preferred methods of surgical stapling is surgical staplers activated by pneumatic feed lines. These surgical staplers provide repeatable ascertainable levels of stapling force so that all users are able to actuate and perform surgical stapling procedures, in especially hard to reach or awkward positions where manual actuation may be difficult, or even impossible.

Nonetheless, previous pneumatic stapling devices have shown certain drawbacks which have proved difficult to correct. Among these are the lack of remote or automatic pin placement. The retaining pin is utilized to contain tissue and provide alignment between the stapling cartridge and the anvil during tissue compression. On pneumatic stapling devices it has proven difficult to create remote pin placement through a pneumatic system. Yet, current retaining pins have been difficult to use, as their clearance may interfere with tight spaces in the body cavity.

Similarly, because there are different tissue thicknesses, it is desirable to provide a pneumatic stapler which has adjustable staple height mechanisms. In this way, each stapler is capable of accomodating varying tissue thicknesses.

Third, pneumatic stapling devices have not been able to provide a system whereby the stapling head has a controlled closure of the head onto the tissue. In previous devices, during tissue compression, the pneumatic pressurization of any compression bladder had the potential for rapid closure of the head without careful control of the supply pressure. In some instances, even careful control could not prevent rapid closure.

Because these staplers are desired to be reloadable, it is desirable to create a system whereby depressurization of the instrument is accurate and repeatable and affords the user the capability of removing a stapling cartridge and replacing it with a fresh cartridge for continued tissue stapling purposes.

Particularly important with limited access applications is the size of the anvil. Because the staples must be emplaced onto an anvil for closure, there must be a mechanism behind the tissue to be closed. The smaller the anvil head can be made, the more versatile the stapler becomes.

SUMMARY OF THE INVENTION

Therefore, it is an object of the invention to provide a pneumatic stapler which contains a mechanism capable of remote or automatic pin placement.

It is further an object of the invention to provide a penumatic surgical stapler which has means for accomplishing adjustable staple height during tissue clamping.

It is further an object of the invention to provide a pneumatic surgical stapler which restricts rapid uncontrolled closure of the stapling head onto tissue.

It is further an object of the invention to provide a return mechanism allowing for reloadability of a pneumatic surgical stapling instrument.

It is further an object of the invention to provide a reduced anvil size to increase the versatility of the invention.

It is further an object of the invention to provide two articulating connections for ease of placement of the instrument in the surgical site. The first articulating connection should be universal, to limit the number of the components involved. The second connection should be a combination of mechanisms offering rotation and articulation of the head in two discrete locations, to increase the reliability of locking of the system.

It is further an object of the invention to provide two retaining pin placement systems. The first system should be automatic and mechanically linked to the pressurization of the instrument. The second, system is remote, and manual and curved in shape, to reduce the size of the stapling head.

These and other objects of the invention are accomplished within a pneumatic stapler which contains a mechanism for automatic pin placement. This retaining pin is connected to a set of linkage plates actuable by a series of inflation of compression bladders in order to create tissue closure and simultaneously create pin placement. Further, because this system has a ramped staple closure mechanism, adjustable staple height is derived. Closure of the mechanism is provided with a detent spring which allows for controlled closure of the tissue during compression. Upon stapling, the stapling head encounters an anvil with reduced size which is kept closed by a latched retaining pin system which allows for controlled width of the anvil so that the stapling head becomes more versatile. Finally, after firing the staples, the mechanism is capable of rapid depressurization so that it may be reloaded and refired by use of a replaceable cartridge.

These and other objects of the invention are better understood by the attached Detailed Description of the Drawings taken in conjunction with the Detailed Description of the Invention.

DETAILED DESCRIPTION OF THE DRAWINGS

FIG. 3 is an exploded perspective view of the head;

FIGS. 3a, 3b and 3c are a view of a retaining pin placement mechanism as seen in the present invention;

FIGS. 7a and 7b are partially cut away views of a latching mechanism as used in the anvil of the present invention so as to reduce anvil head size;

FIG. 9 is an exploded view of the shaft;

DETAILED DESCRIPTION OF THE INVENTION

Figure 1:
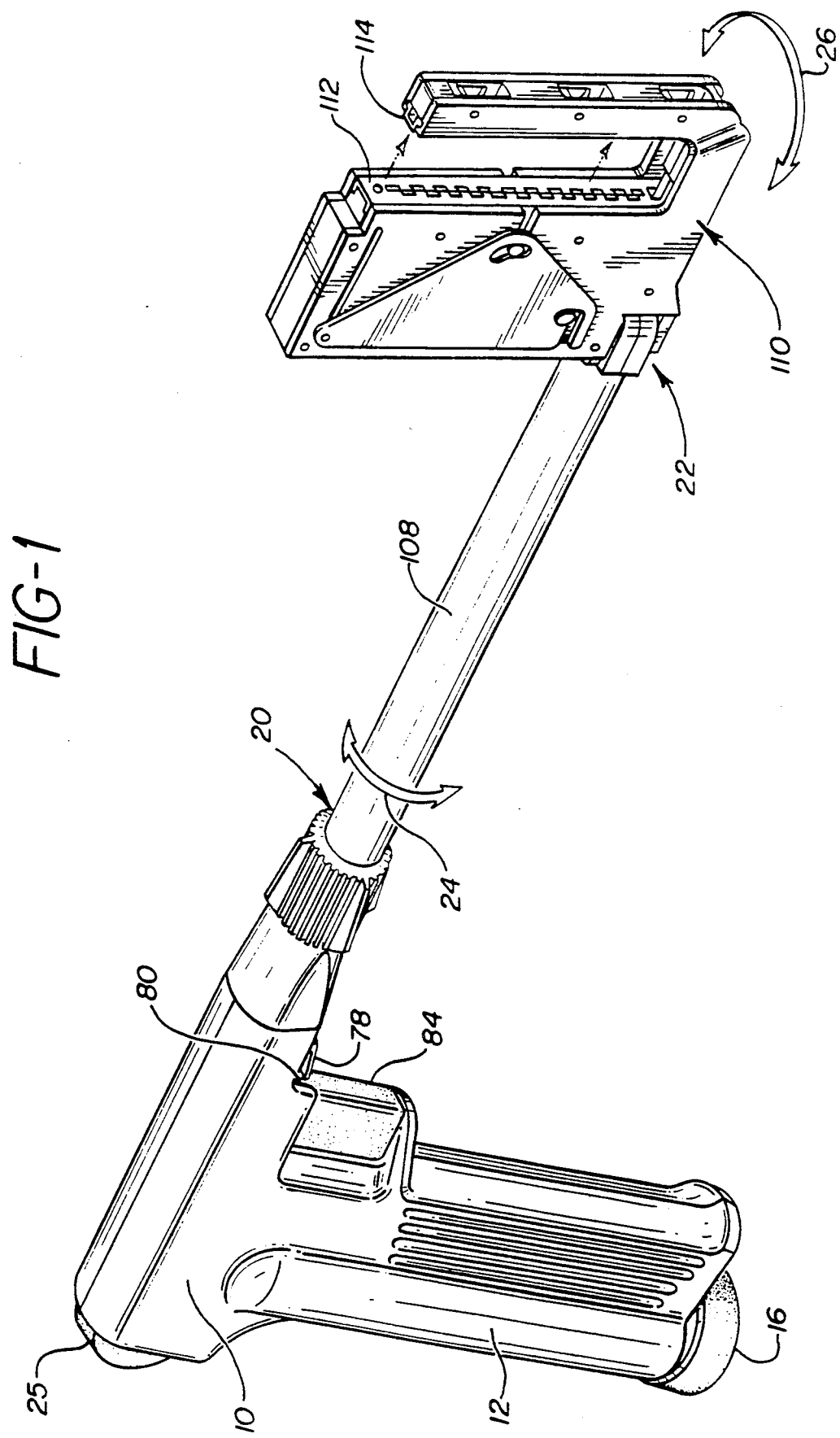
FIG. 1 is a perspective view of a pneumatic surgical stapling device.

Referring first to FIG. 1, a pneumatically actuated surgical stapler of the present invention is shown. The stapler includes three major components: a handle portion 10, a shaft portion 108, and a stapler head 110. Also located at the joints 20 and 22 are manually rotatable unions which allow free rotation of the major components of the stapler with respect to each other, as indicated by the arrows 24 and 26. Specifically, the shaft 108 is free to rotate up to about 340° about its axis at the joint 20 as indicated by arrow 24. The stapler head 110 is free to rotate greater than 200° about an axis which is normal to the axis of the shaft 108, as indicated by arrow 26.

A cylinder of pressurized gas is inserted into the lower portion 12 of the handle 10 by removing the cap 16 and inserting the cylinder into the handle. Once the cylinder has been inserted and the cap 16 tightened, gas from the cylinder is released and flows to a pressure regulator in the handle. The release of gas from the cylinder is achieved by acting on the thumbwheel or slide 25 at the rear of the handle.

The first step in a stapling procedure is to clamp the tissue to be stapled between the jaws of the stapler head 110. The tissue is located between the jaws, and thumbwheel or slide 25 which extends from the rear of the stapler is pushed upward. When the slide 25 is pushed, pressurized gas is allowed to flow to the stapler head through a first gas line to clamp the tissue between the jaws of the stapler head.

Staples in a cartridge 112 may then be driven through the clamped tissue by depressing the trigger 84 of the handle. Before the trigger can be depressed, however, a trigger safety 78 must be moved from the position shown in FIG. 1. This safety mechanism prevents inadvertent placement of the staples before the user is ready to do so. After the trigger safety 78 has been moved up, the trigger may be depressed to implant the staples in the tissue, either by clinching the legs of the staples against an anvil 114 in the stapler head 110 or by interlocking the legs of the staples with connecting staple receivers located in the anvil. Optionally, as trigger 84 is depressed, the trigger safety can be rotated back to its more vertical position and reset by sliding in slot 80 by spring force.

Figure 2:
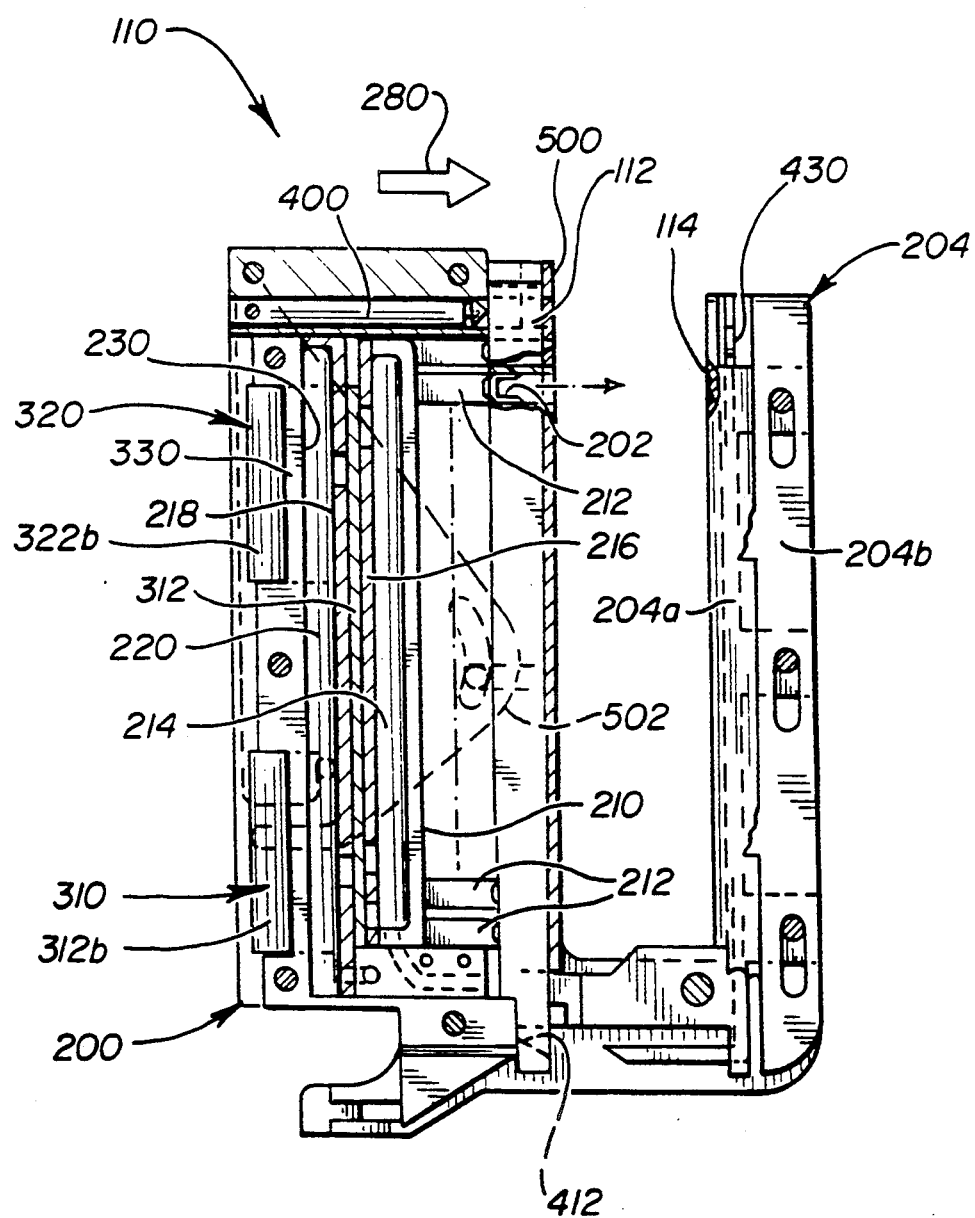
FIG. 2 is a cut away plan view of a pneumatic surgical stapling device head.

FIG. 2 is a partial cross-sectional illustration of the stapler head 110 of the present invention. The stapler head includes a jaw 200 which carries a plurality of staples 202 in a movable clamping and stapling mechanism. Opposite the jaw 200 is a stationary opposing jaw 204. The face of the stationary jaw which opposes the stapling mechanism comprises an anvil which clinches or bends the legs of metal staples which pass through the tissue between the jaws. Alternatively, when the staples are formed of absorbable polymeric materials, the stationary jaw carries a cartridge of receivers which mate with and retain the legs of the polymeric staples. Such polymeric staples and receivers are describes in U.S. patent application Ser. No. 117,592, filed Nov. 5, 1987, now U.S. Pat. No. 4,805,617.

The staples 202 are located in pockets formed in a staple cartridge 112 on the jaw 200, with the legs of the staples directed toward the stationary jaw 204. Behind the staple cartridge 112 is a staple pusher 210. The staple pusher has fingers 212 which are directed toward the crowns of respective staples in the staple cartridge. Behind the staple pusher 210 is a driver bladder 214. The driver bladder is located adjacent a clamping bladder 220. The clamping bladder 220 is located inside a housing 230.

When tissue to be stapled is located between the jaws 200 and 204 of the stapler head and it is desired to clamp the tissue between the jaws, the slide 25 is moved out of line and pressurized gas flows from the handle and into the head 110. Gas is forced into the clamping bladder where it expands and pushes the driver forward (as indicated by the arrow 280) and toward the stationary jaw. As the clamping bladder moves, it carries the driver bladder, staple pusher, and staple cartridge with it. This will clamp the tissue between the staple cartridge and the stationary jaw 204.

As seen especially in the exloded view of FIG. 3, with the tissue securely clamped between the jaws, the user releases the trigger safety and pulls the trigger to implant the staples. The expanding gas in this space pushes the driver bladder 214 forward against the rear of the staple pusher 210, whereby uniform pressure is applied to the pusher and its fingers. The fingers then drive the staples out of the pockets of the staple cartridge, through the tissue, and against the anvil or into the receivers of the stationary jaw. When the trigger is released, the pressurized gas to the driver piston and clamping piston is vented through the handle, releasing the jaw 200 from the stapled tissue.

A pneumatic pressure regulation system suitable for the development of pressure-regulated gas for operation of the stapler head of the present invention is described in concurrently filed United States patent with U.S. Pat. No. 4,951,861, entitled "SURGICAL STAPLER PRESSURE REGULATOR."

1. Staple Height Adjustment

Different human internal organs have different tissue thicknesses. It is therefore desirable to have different staple heights that will accomodate these different tissue thicknesses. For this reason, the stapler head 110 is designed with a staple height adjustment mechanism that will provide three discrete staple heights. These heights correspond to 1.2, 1.6, and 2.0 mm inside staple dimensions.

Figure 4:
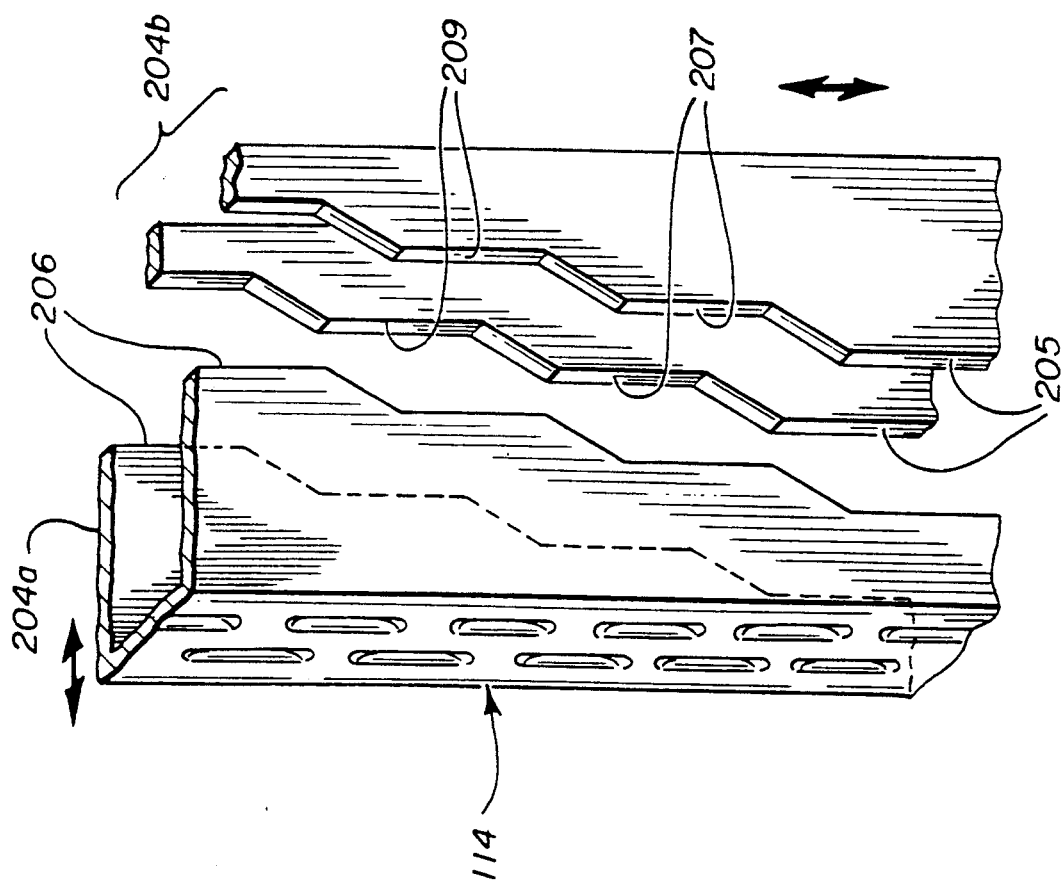
FIG. 4 is a perspective partially cut away view of an anvil height adjustment mechanism as seen in the invention.

As seen in FIG. 4, adjustable staple height is accomplished by means of an anvil 204a that moves parallel with respect to jaw 200. Parallel movement is initiated by the perpendicular movement of a ramped gap adjust plate 204b that is moved up and down by means of a thumb switch not shown located on the bottom of the instrument. The thumb switch projects between a pair of retaining hooks, and can be activated from the bottom of the instrument.

There are ramped projections 205,207,209 on the top of the gap adjust plate 204b. These projections fit into corresponding ramped cutouts in the anvil 204a. Perpendicular movement of the gap adjust plate 204b with respect to the anvil 204a results in the plate projections engaging in different ramp surfaces in the anvil cutouts. The cutouts are dimensioned such that the desired staple heights can be achieved through the appropriate projection/ramp combination. Movement of the anvil 204a must be perpendicular to the stapler pockets since the staple pockets which clamp staples must always be aligned with matching drivers 212 and staples in the cartridge channel assembly. This is accomplished by means of grooves 206 in the anvil 204a which fit into posts which serve to contain the anvil and permit only perpendicular anvil movement.

Design of the channel and hooks is such that cartridge 112 will always come into the same relative position on the hooks. This is accomplished by means of positive stops at the front and back of the stapler cartridge such that height adjustment is therefore independent of the hooks and cartridge 112 and relies only on anvil 204a position.

2. Closure Detent Mechanism

Figure 5:
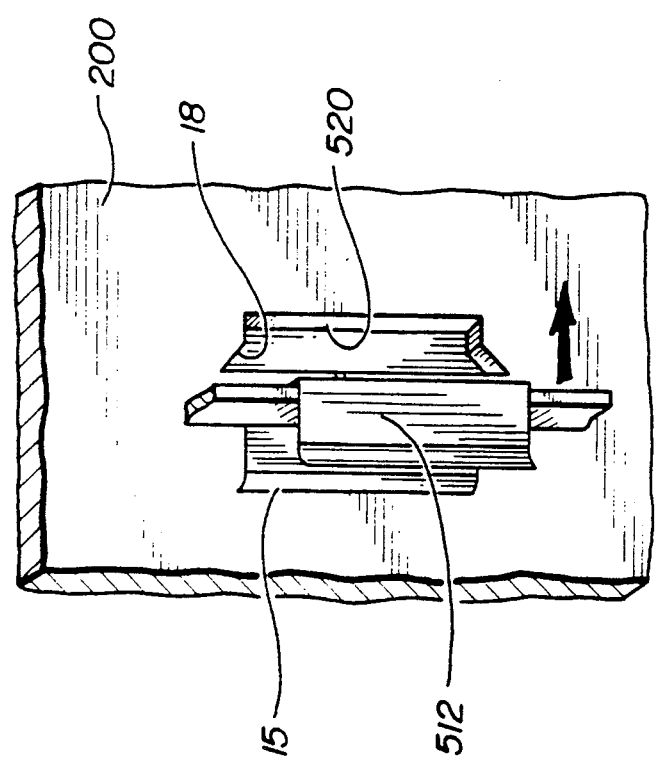
FIG. 5 is a detent spring mechanism of the invention allowing for controlled compression closure set at an intermediate detent position.

It is desirable to maintain control of closure of the jaws 200, 204 during tissue compression. The carbon dioxide pressurization of clamping bladder 220 may close stapler head 110 too rapidly if supply pressure is not carefully controlled. A mechanism is therefore provided to stop clamping movement after approximately 0.275" of closure. As seen in FIG. 5, the mechanism comprises a detent spring 512 with a lip 15 projecting from its channel. This lip 15 drags against the inner walls of the stapler head until it encounters ledge 520 in jaw 200. The spring 512 locks on the ledge 520 and restricts further travel of clamping mechanism until such time as sufficient pressure is generated in the bladder 220 to push spring 512 over ledge 520. At this point bladder 220 continues to expand and jaw 202 continues to close.

The detent spring is activated by pressurization in the compression channel of jaw 200. Spring 512 is positioned between jaw 202 and bladder 220. Inflation forces the lips 15 of the detent spring 512 outward, insuring engagement with ledge 520. Spring 512 is positioned so lift 15 rides against wall 202, as seen in FIG. 5. Spring 512 is designed so that, in its relaxed state, it will contract to some neutral, resting configuration. This avoids drag and binding on the jaw 200 during deflation and when the bladder 220 returns to its resting position. A lead-in ramp 18 in the ledge 520 permits gradual engagement of the spring 512 during compression and avoids causing the spring 512 to become caught in the wall of jaw 202 during deflation.

3. Return Mechanisms

Closure and firing of the instrument are accomplished through pressurization of the latex bladders. Depressurization of the instrument does not, however, result in return of the driver 214 or compression mechanisms. It is therefore necessary to provide additional systems to achieve return of these closure mechanisms. Not only is this desirable for instrument reloadability but it provides further insurance from a safety standpoint. The instrument is therefore configured to default to an open position in the event of lack of pressure for cycle completion or other instrument failure.

Inflation results in pushing the clamping bladder 220 into the staple cartridge 112 and forming staples 202 against the jaw 204. As in FIGS. 3 and 6, two constant force springs 310, 320 are positioned in jaw 200 between the bladder compression channel 218 and bladder 220. These springs 310, 320 extend by scrolling sections 312a, 312b away from face 312 and sections 322a, 322b away from face 322 during inflation of clamping bladder 220; springs 310, 320 return to their original position when the bladder 220 is deflated. 310, 320 extend by scrolling sections 312a, 312b, 322a, 322b during inflation of clamping bladder 220 and return to their original position when the bladder 220 is deflated. This results in the compression channel being pulled back against the deflated bladder 220 and permits removal and reloading of the cartridge 112.

Figure 6:
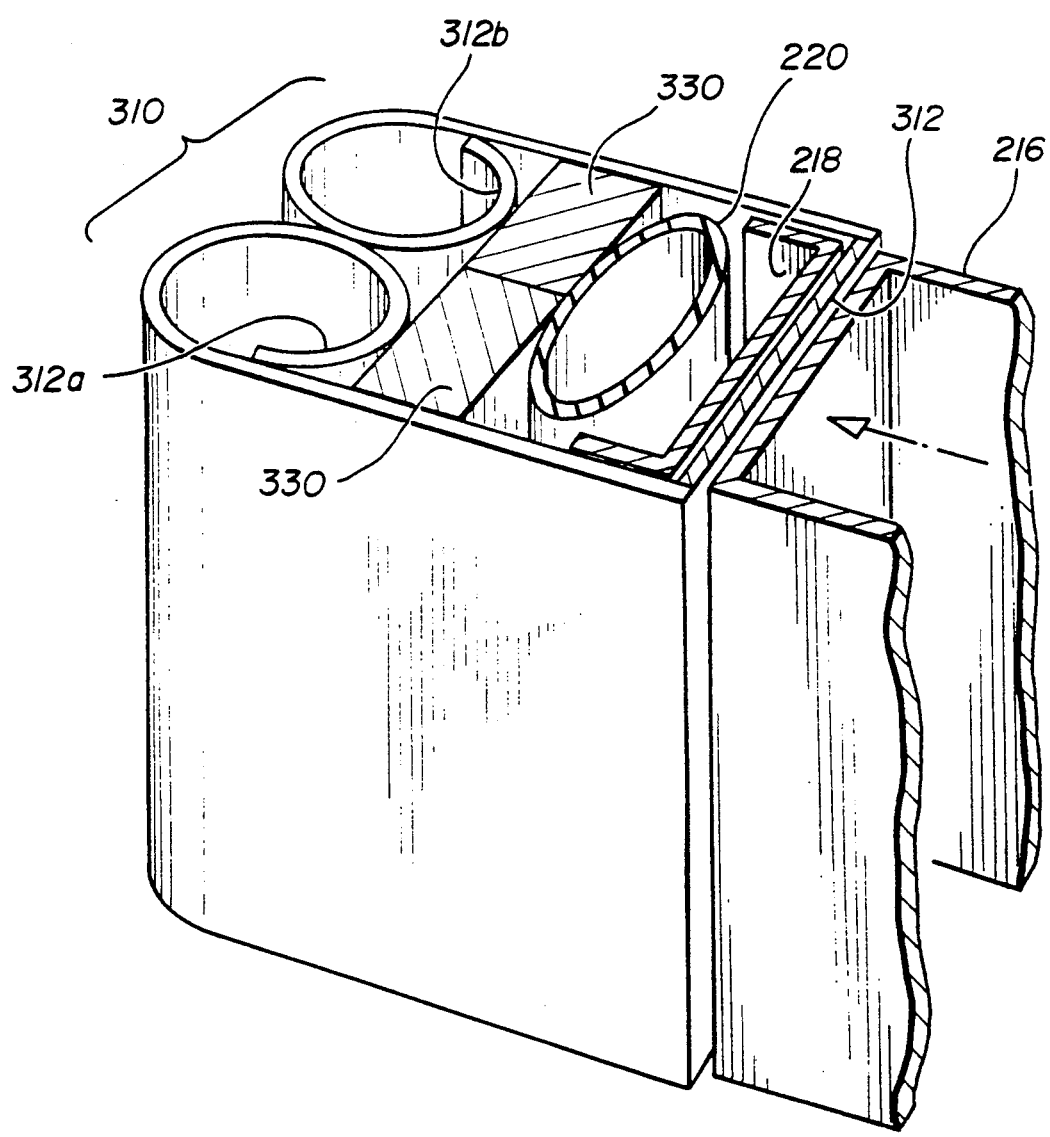
FIG. 6 is a return spring mechanism allowing for a rapid decompression and reloading of a stapling cartridge in the present invention.

As seen in FIG. 6 one of these identical "constant force" springs 310 has a cylindrical coil of material anchored over the top of the compression backing plates 330. The flat, base portions 312 of the spring is trapped between the cartridge channel 216 and compression channel 218. Inflation of the bladder 220 results in movement of the compression member 330, which in turn lengthens or uncoils the scroll sections 312a, 312b of "constant force" spring 310. The spring resists the inflation and pulls the compression channel when the bladder 220 is deflated. The force to close the instrument due to increasing drag between the springs and the bladder side walls as pressure is increased is nonlinear and therefore provides a means for controlling jaw closing during pressurization.

In the absence of the springs 310, 320, introduction of pressure to the bladder 220 would result in immediate closure of the jaw clamping mechanism, as there would be nothing to restrict uncontrolled movement. The increasing drag of the springs 310, 320 permits the user to stop the jaw closure at any point throughout compression and open head 110. With adequate control of the pressure in the instrument handle 120, it is therefore possible to control jaw clamping mechanism closure throughout the entire closure cycle.

4. Anvil Latching Mechanism

In limited access applications, the size of the anvil or jaw 204 is particularly important as the anvil size can be the principal restriction to instrument access. As seen in FIGS. 3a, 3b, 3c and 7, a mechanism is designed which reduces the overall size of the anvil 114 by changing it from a cantilever beam to a beam simply supported on its distal end. This permits a substantial reduction in the cross-sectional area of the anvil 114 at its bottom and rear of the member.

As seen in FIGS. 7a and 7b, a latching retaining pin 400 is utilized to reduce the size of the anvil 114. The retaining pin 400 has a groove 410 cut around the end of the pin 400 near its tip 402. A ledge 430 positioned under the anvil 114 engages groove 410 of pin 400 when the pin 400 is properly positioned in the anvil 204. Movement of the latch 400 is accomplished by means of the motion of the staple cartridge 112 during clamping bladder 220 inflation. As seen in conjunction with FIG. 3, a ramp 412 at the lower portion of the cartridge 112 moves towards ledge 430 and forces the rear of ledge 430 upward toward pin 400. 412 in the rear slot of the cartridge 112 forces the latch upward. Latching does not occur until the pin 400 is adequately placed in the anvil 114. Latching is accomplished as soon in the closure cycle as possible so as to support the end of the jaw 204 before tissue compression causes deflection of jaw 204.

5. Remote, Automatic Pin Placement

A retaining pin is utilized to contain tissue and provide cartridge/anvil alignment and support for the anvil during tissue compression. As in FIGS. 3a, 3b and 3c, a remote, automatic pin placement system is disclosed. Inflation of the bladder 220 results in movement of a compression channel 218 and a cartridge channel 216, as from FIG. 6. Cartridge retaining pins or screws 501a, 501b are connected to a pair of linkage plates 502 through a slot 503 and placement hole 508 and through jaw assembly 200 to cartridge 500, causing plates 502 to move along with cartridge 500, as can be seen in FIGS. 3a, 3b, 3c. The design of slot 503 and position of slot 503 and pin 400 are such that they determine timing for the mechanism. The linkage plates 502 are pivoted from the instrument hooks 504 via hook screws 505 and are attached to the tissue retaining pin 400 using threaded nuts, "E-rings", or similar fastening devices.

First, as the channel 500 moves, the linkage plates 502 pivot around the hook screw 505. As can be seen in FIGS. 3a, 3b and 3c, the pins 501a, 501b are guided in channels 503, 518 respectively. When bladder 220 inflates, cartridge channel 216 is caused to move toward anvil 204. This in turn causes pin 400 to move forward. Pin 400 causes pin 501b to be guided in slot 518. Motion of pin 501b causes rotation of plates 502 on either side of jaws 200. Then, the furthest tip of the plates 502, attached to the retaining pin 400, is forced to move toward the anvil 114. The rate of retaining pin 400 travel is determined by the ratio of the hook screw 505/retaining pin 400 moment arm to the hook screw 505/channel screw 400a moment arm. The pin 501 force capabilities are also determined by this ratio. The ratio has been designed to provide retaining pin 400 speed approximately three times that of the channel 500. This insures that the retaining pin 400 will be placed in the anvil 114 by the time tissue compression takes place.

As an example, pin 400 is placed during the first 0.275" of cartridge channel 500 travel. The pin 501 must then stop, and remain in position during the last 0.325" of cartridge 500 travel. This means that linkage plates 502 must become inoperative after the first 0.275" of cartridge channel 500 movement. Of course, other combinations are forseeable and are intended to be included within the scope of the invention. This is accomplished by changing linkage plate 502 pivot points. During the first portion of travel, the linkage plate 502 pivots around the hook screw 505 in a traverse portion of the groove 504. Once the pin 400 is placed, the retaining pin 501 becomes the linkage 502 pivot. The hook screw 505 then falls into the stationary portion of the groove 507. During this portion of closure, the linkage plate 502 drops down without moving retaining pin 400.

6. Shaft with Articulating Connection

Figure 8A:
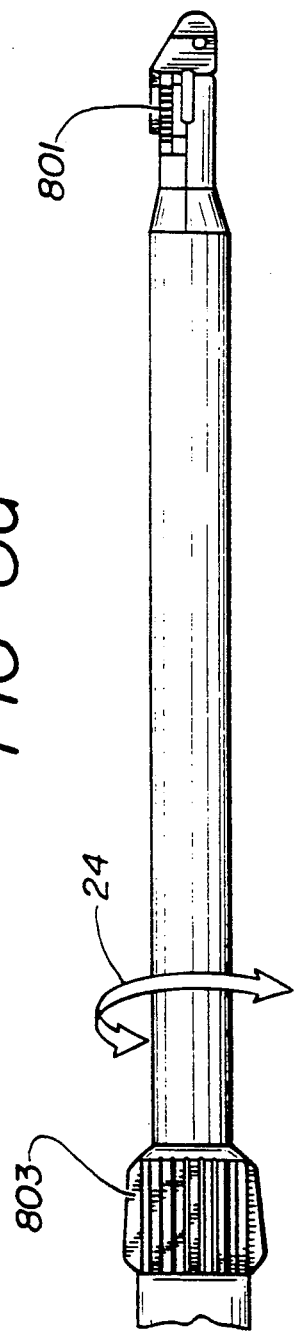
FIGS. 8a and 8b are cut away views of the shaft with articulating connection for allowing ease of placement of the head of the instrument.
Figure 8B:
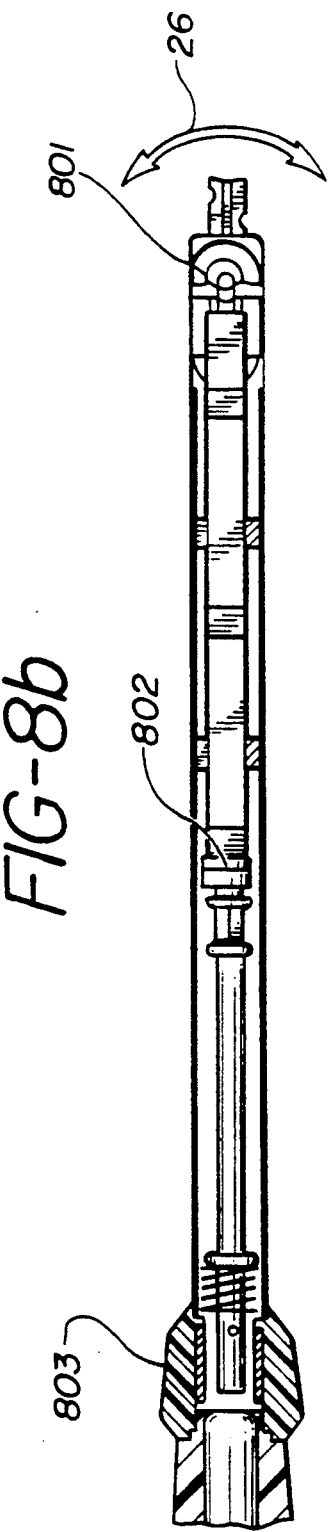

A shaft is used to connect the handle to the head of the instrument to facilitate insertion of the instrument in the surgical site, two means of articulation and rotation are shown in FIGS. 8a, 8b, 9 and 10. FIGS. 8a, 8b and 9 show locations of articulation 801, as by arrows 26, and rotation 802 as shown by arrow 24. A lock 803 is activated to fix the desired location of the head after rotation or articulation.

Figure 10:
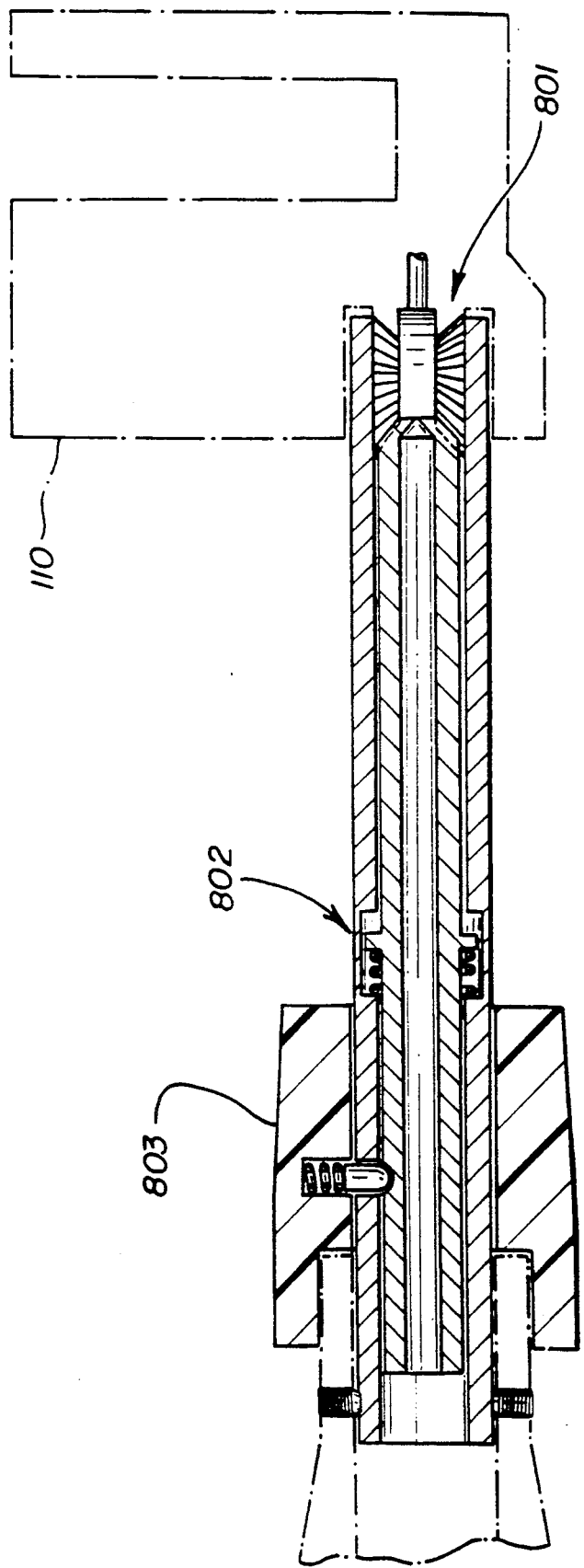
FIG. 10 is a plan view of the universal articulating connection.

FIG. 10 shows a universal articulation/rotation mechanism which can be used interchangeably with one of the previously described mechanisms shown by FIGS. 8a, 8b and 9. Importantly, in this mechanism there is a limited number of parts for connection and the ability to keep the shaft and handle components fixed while rotating or articulating the head. As shown, all the universal part of the mechanism are contained on the head. This system also has a lock which deters overcoming the desired position of the head when locked.

7. Manual, Remote and Curved Retaining Pin

Figure 11:
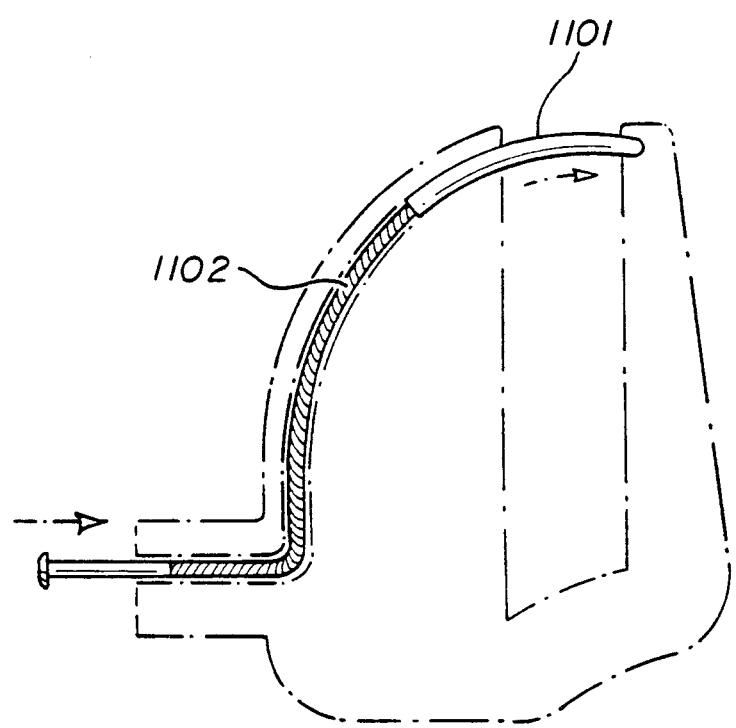
FIG. 11 is a plan view of the curved, manual inserted retaining pin mechanism.

FIG. 11 shows the use of a manually activated retaining pin 1101, with a flexible shaft 1102 to transmit the motion of pin 1101 through a curved path. The use of this retaining pin 1101 allows the operator to insert the instrument in difficult areas where corners and other protuding elements could be detrimental to instrument insertion and use.

This invention has been described in conjunction with a particularly preferred embodiment. It is to be understood that the invention is next to be encompassed by the attached claims and then equivalents.

What is claimed is:

1. A surgical stapler comprising:
   a shaft defining a longitudinal axis and containing a cartridge holding a plurality of staplers;
   an anvil;
   a plurality of drivers slidable parallel to said longitudinal axis, said drivers capable of driving said staples into said anvil;
   a retaining pin extendable from said cartridge into said anvil, said retaining pin capable of holding tissue between said cartridge and said anvil;
   means for remote placement of said retaining pin into said anvil comprising a plurality of linkage plates, said linkage plates attached to said cartridge by a plurality of pivot screws such that said linkage plates cause movement of said cartridge such that said retaining pin is moved relative to said cartridge; and
   actuating means capable of actuating said linkage plates.

2. The stapler of claim 1 further including an anvil adjustment mechanism attached to said stapler and capable of positioning said anvil with respect to said staples whereby an adjustable staple height is derived.

3. The stapler of claim 2 wherein said adjustment mechanism comprises a series of ramps operable with respect to said anvil during adjustment of said stapler.

4. The stapler of claim 1 wherein said actuating means comprise a series of compression bladders.

5. The stapler of claim 4 further comprising a latch, said latch capable of holding said retaining pin in place during compression of said bladders.

6. The stapler of claim 5 further comprising constant force spring means capable of exerting force on said anvil with respect to said bladders whereby said stapler is opened to separate said anvil and said bladder by means of said constant force spring means.

7. The stapler of claim 1 whereby said retaining pin follows a curved path.

* * * * *